(12) United States Patent
Morris et al.

(10) Patent No.: US 6,629,955 B2
(45) Date of Patent: Oct. 7, 2003

(54) MEDICAL INSTRUMENT FLOW STOP INTERFACE

(75) Inventors: Matthew G. Morris, San Diego, CA (US); Victor R. Hurtado, San Diego, CA (US)

(73) Assignee: ALARIS Medical Systems, Inc., San Diego, CA (US)

( * ) Notice: Subject to any disclaimer, the term of this patent is extended or adjusted under 35 U.S.C. 154(b) by 0 days.

(21) Appl. No.: 09/848,790

(22) Filed: May 4, 2001

(65) Prior Publication Data

US 2002/0165503 A1 Nov. 7, 2002

(51) Int. Cl.[7] ............................ F04B 53/00; A61M 1/00
(52) U.S. Cl. ........................................ 604/153; 417/234
(58) Field of Search .............................. 604/250, 249, 604/153, 256, 131, 34; 251/7; 417/63, 53, 234, 276

(56) References Cited

U.S. PATENT DOCUMENTS

| | | | |
|---|---|---|---|
| 4,460,358 A | | 7/1984 | Somerville et al. .......... 604/250 |
| 4,689,043 A | | 8/1987 | Bisha .......................... 604/250 |
| 5,453,098 A | * | 9/1995 | Botts et al. ..................... 251/7 |
| 5,478,211 A | | 12/1995 | Dominiak et al. ........... 417/234 |
| 5,482,446 A | * | 1/1996 | Williamson et al. ........ 417/234 |

* cited by examiner

Primary Examiner—Michael J. Hayes
Assistant Examiner—Roz Ghafoorian
(74) Attorney, Agent, or Firm—Fulwider Patton Lee & Utecht, LLP

(57) ABSTRACT

A fluid infusion pump includes a platen between an outer door and the pumping mechanism. The platen is located so that as the outer door of the pump is moved to the closed position, it moves the platen to position the fluid flow tube into occlusive contact with the pumping mechanism before the platen engages a flow stop formed integrally with the tube and releases the flow stop to permit fluid flow, thus avoiding a free flow condition. The door also includes a handle having a sear with a hook that engages the flow stop when the door is in the closed position. As the door is opened, the hook moves the flow stop to the occluded position before the platen is moved away from the tube thus preventing a free flow condition. The platen includes a flow stop release portion that is offset from the remainder of the platen that operatively engages a release tab on the flow stop to permit movement of the flow stop to the fluid flow configuration. The platen is mounted to the housing with a floating hinge and datum pins located on the face of the pumping mechanism precisely locate the platen into position with the pumping mechanism and thereby result in precise positioning of the fluid tube.

54 Claims, 12 Drawing Sheets

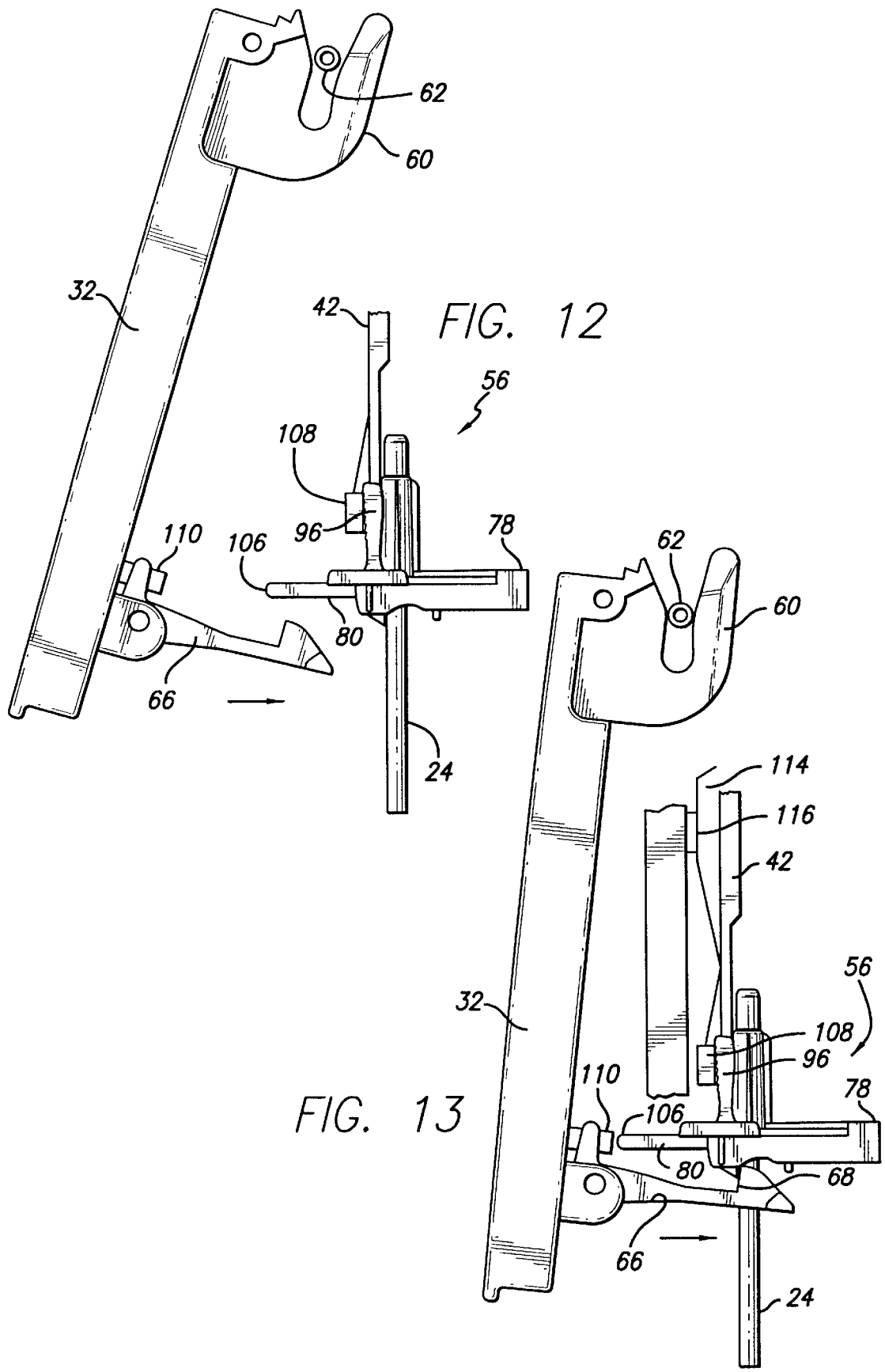

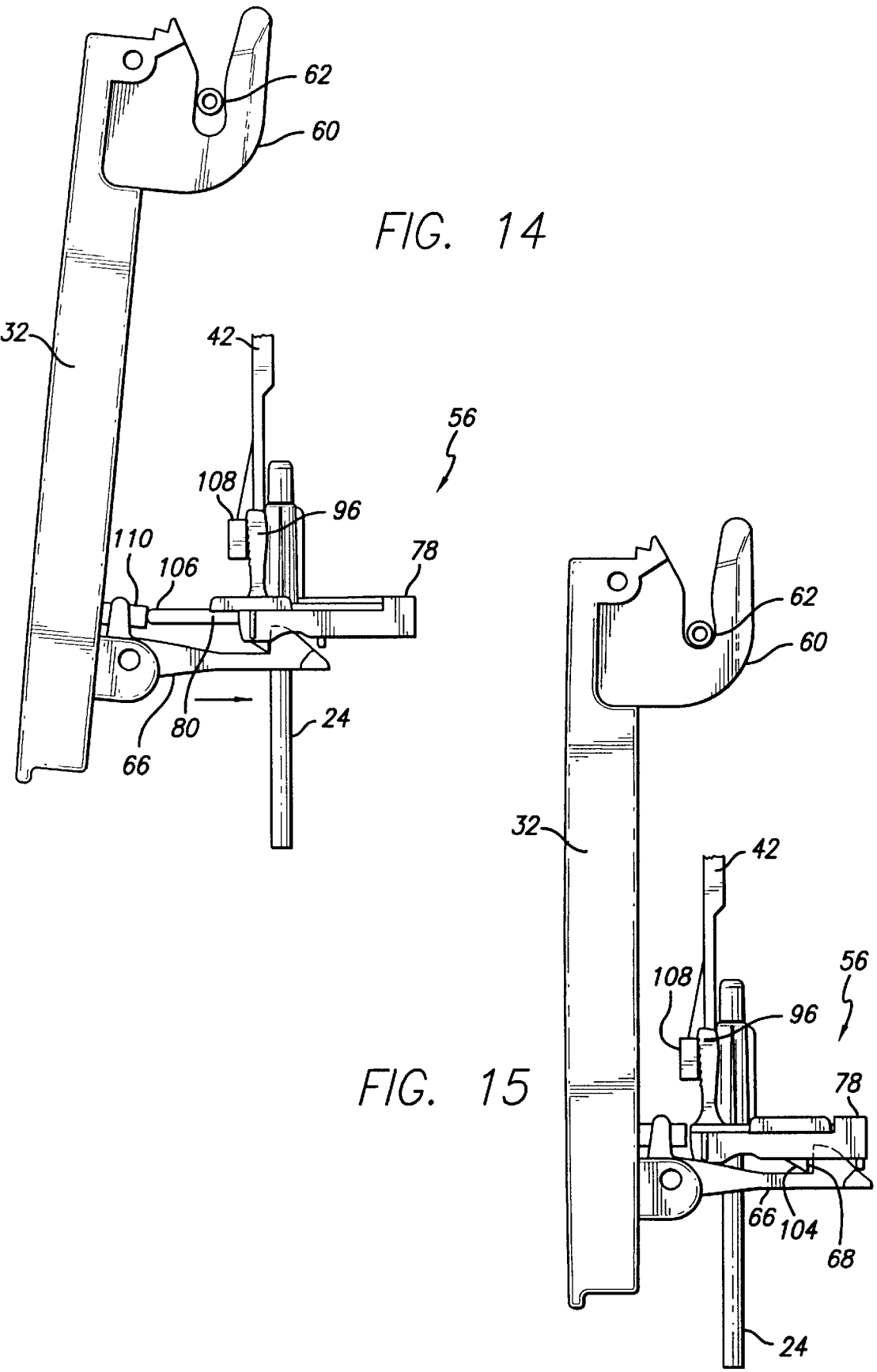

MEDICAL INSTRUMENT FLOW STOP INTERFACE

The invention is generally related to the field of intravenous ("IV") infusion devices such as infusion pumps and the associated flexible IV tubing and flow stop devices, and more particularly, to devices used to prevent free flow in an IV tube when the infusion pump is disengaged from the IV tube.

BACKGROUND

It is a common practice to deliver fluids such as medications to a patient intravenously by means of a pumping device such as a "four finger" pump or a peristaltic pump. Such pumps are useful because they can deliver the medication in a highly controlled fashion, and because they do so without coming in contact with the medication. The fluid is moved through a flexible IV tube by pressing a pumping member against the outer surface of the tube sufficiently to force fluid downstream through the tube into the patient.

Both a four finger pump and a peristaltic pump operate by occluding the tube at all times so that there can be no free flow or uncontrolled flow between the fluid reservoir and the patient. In the case of a four finger pump, either an upstream valve finger or a downstream valve finger occludes the tube at all times. In the case of a peristaltic pump, at least one of the peristaltic fingers is at all times occluding the tube.

It is common for the pumping mechanism to be disposed in a housing with a hinged door. The tube through which the fluid is to be moved is placed in contact with the pumping mechanism inside the door, with the upstream and downstream ends of the tubing typically extending out the top and bottom, respectively, of the door opening. As the door is shut over the tube, a platen presses against the IV tube to provide a backing surface against which the pumping members can occlude the tube.

This arrangement of the IV tube relative to the pumping mechanism requires that there be some means for preventing flow in the tube when the door is open. Otherwise, during the process of mounting or removing the tube from the pumping mechanism, an unwanted flow of fluid could occur in the IV tube. This could result in the uncontrolled infusion of medication into the patient under the influence of the static head pressure in the tube. Known devices for preventing unwanted flow in the tube include manual clamps separate from the infusion pump, and automatic occluding devices mounted on the pump.

The manual clamp devices require some manipulation skill on the part of the attending technician, and there is the chance that the technician will forget to properly time the occlusion of the tube relative to the opening of the door on the pumping device. Furthermore, the door may be accidentally opened which could result in free flow in the tube.

The automatic flow stop engagement system disclosed in U.S. Pat. No. 5,453,098 has been a major advance in the art. However, in the case where the hinge or hinges of the door of the pump must be moved forward so that the pump has a narrow profile and can be placed closely beside another medical device without interfering with that device when the pump door is opened, such a door may not be squared with the tube. When the platen is mounted to the inner surface of the door, it may apply an undesirable rolling force to the tube when the door is opened and closed. Such a rolling force may stress the tubing any may move the tube out of the correct position in relation to the pumping mechanism and the automatic flow stop feature provided by the pumping mechanism may not be present because the tube is out of position. Typically, the action of opening the door is relied on to initiate the occlusion of the IV tube by the clamp and the action of closing the door is relied on to initiate the release of the IV tube from the clamp. Therefore, free flow of fluid could occur if the door is not located properly in relation to the tube. However, for purposes of ease in automatically controlling the clamp on the tube by the actions of the door opening and closing, it is desirable that door continue to effect such clamp control.

In designs where an engagement device such as a hooked arm is formed as part of the door and which engages the flow stop to move it to the occlusion position before the door permits disengagement of the pumping mechanism with the tube, it would be desirable to provide a warning to medical treatment personnel if the engagement mechanism is not in the correct position before the door is opened. A manual clamp could then be applied to the tube before the door of the pump is opened.

Therefore, those skilled in the art have recognized a need for an apparatus that will automatically and positively occlude an IV tube before the pumping mechanism is disengaged from the tube. A need has also been recognized for an apparatus that will automatically and positively maintain the IV tube in an occluded state until after the pumping mechanism is engaged with the tube and will then move the flow stop to a flow configuration. A need has also been recognized for an apparatus that will perform the above-discussed operations on the tube with a door that has been mounted in a more forward position to accommodate the placement of the pumping apparatus in close proximity to other medical devices. A further need has been recognized for a detection system that will determine if a flow stop engagement device is present with the pump door and will provide an alert if the engagement device is not detected. The present invention fulfills these needs and others.

SUMMARY OF THE INVENTION

The present invention is directed to avoiding the free flow of fluid through a medical instrument by judicious operation of a flow stop in conjunction with instrument loading and unloading operations. With more particularity, a platen is used to control a flow stop coupled to a tube so that movement of the door of the medical instrument controls the configuration of the flow stop.

In one aspect in accordance with the invention, an apparatus is provided for controlling a flow stop to reside in an occluding configuration at which the flow stop occludes a resilient tube and to reside in a flow configuration at which the flow stop permits flow through the resilient tube by the position of a door that is mounted with a first hinge to the housing of a medical instrument, the apparatus comprising a base on the flow stop for holding the resilient tube, a slide clamp slidably mounted on said base and engaging the tube, the slide clamp adapted for movement between the occluding configuration and the flow configuration, and a platen mounted in relation to the housing with a second hinge, the second hinge located at a position different from the position of the first hinge but such that the platen is disposed between the door and the slide clamp of the flow stop wherein moving the door towards the housing engages the platen causing it to engage the slide clamp to move the slide clamp to the flow configuration whereby fluid may flow through the tube.

In more detailed aspects, the platen comprises a body portion and a flow stop actuator portion disposed as an extension of and offset from the body portion of the platen such that the body portion of the platen engages the tube against the medical instrument while being pivoted into position by the movement of the door and the actuator portion contacts the flow stop before the slide clamp may be moved to the open position. Further, the flow stop comprises a locking arm engaged with the slide clamp that prevents the slide clamp from being moved to the flow configuration, and the flow stop comprises a release tab connected to the locking arm that disengages the locking arm from the slide clamp when the release tab is moved to a released position, wherein the flow stop actuator portion of the platen is disposed so as to contact the release tab of the flow stop and move it to the released position before the slide clamp is moved to the flow configuration.

The medical instrument also includes datum pins located at selected positions on the instrument, the pins having a predetermined length selected so that when the platen is engaged with the pins, the platen will have a known location in relation to the medical instrument and wherein the length of the datum pins is selected so that the flow stop actuator portion of the platen will contact the release tab of the flow stop, in other aspects. Further, the second hinge of the platen comprises a floating hinge adapted to permit the platen to be located in contact with all the datum pins when the door engages the platen. Additionally, the platen comprises a plurality of contact datum surfaces disposed on the platen at positions selected to engage the datum pins when the door positions the platen in contact with the datum pins. In further aspects, the platen comprises a load distribution rib located on the platen so as to receive the force or load of the door and distribute that force along the platen. Additionally, the door comprises a pressure surface located on the inside of the door at a location so as to contact the load distribution rib of the platen to press the platen against the datum pins.

In yet further aspects, the housing of the medical instrument comprises an anchor yoke that is biased toward the housing, the door comprises a pivotally mounted handle located to engage and capture the anchor yoke to firmly hold the door in a closed position against the housing, and wherein the anchor yoke is biased towards the housing by an extent that will assure that the door contacts the load distribution rib of the platen thereby forcing the platen into contact with the datum pins. In more detailed aspects, the handle includes a sear with a hook, the sear and hook located so as to engage the slide clamp of the flow stop when the door is in the closed position and to move the slide clamp to the occluding configuration when the door of the medical instrument is opened thereby preventing free flow through the tube.

In yet further more detailed aspects, the apparatus comprises a sear detector located in the medical instrument at a position selected so as to detect the presence of the sear in position in relation to the slide clamp, the detector providing a sear detection signal and a processor connected to the sear detector to receive the sear detection signal and adapted to provide a sear alert signal in the event that the sear is not detected by the sear detector. Further, the sear detector comprises a photo emitter and photo receiver both directed towards a predetermined location for a sear and the sear comprises a photo-reflective surface. The apparatus further comprises a flow stop detector located in the medical instrument at a position selected so as to detect the presence of the flow stop in the medical instrument and configured to provide a flow stop detection signal and a processor connected to the flow stop detector to receive the flow stop detection signal and adapted to provide a flow stop alert signal in the event that the flow stop is not detected by the flow stop detector.

In other detailed aspects, the first hinge is located forward on the housing so that the door is separated from the flow stop when the flow stop is mounted in the medical instrument.

In another main aspect, an apparatus is provided for controlling the flow of fluid through a tube mounted in a medical instrument, the medical instrument including a flow mechanism that engages the tube to precisely regulate the flow of fluid through the tube to a patient, and a flow stop mounted to the medical instrument, the flow stop having an occluding configuration at which the flow stop occludes the tube and a flow configuration at which the flow stop permits flow through the tube, the medical instrument having a housing to which a door is mounted with a first hinge, the apparatus comprising a base on the flow stop for holding the tube, a slide clamp slidably mounted on said base and engaging the tube, the slide clamp adapted for movement between the occluding configuration and the flow configuration, and a platen mounted in relation to the housing with a second hinge, the second hinge located at a position different from the position of the first hinge but such that the platen is disposed between the door and the flow mechanism and the flow stop such that when the door is moved towards the flow mechanism, the door engages the platen causing it to engage the tube against the flow mechanism to occlude the tube by the flow mechanism and then engages the slide clamp of the flow stop to move the slide clamp to the flow configuration thereby avoiding a free flow condition.

In another main aspect, an apparatus is provided for controlling the flow of fluid through a tube mounted in a medical fluid infusion pump, the pump including a pumping mechanism that engages the tube to precisely pump the fluid through the tube to a patient, the tube having a flow stop having a base and a slide clamp slidably mounted on the base and engaging the tube, the slide clamp having an occluding configuration at which the slide clamp occludes the tube and a flow configuration at which the slide clamp permits flow through the tube, the pump having a housing to which a door is mounted with a first hinge, the apparatus comprising a platen mounted in relation to the housing with a second hinge, the second hinge located at a position different from the position of the first hinge but such that the platen is disposed between the door and the pumping mechanism and the flow stop such that when the door is moved towards the pumping mechanism, the door engages the platen causing it to engage the tube against the pumping mechanism to occlude the tube by the pumping mechanism and then engages the slide clamp of the flow stop to move the slide clamp to the flow configuration thereby avoiding a free flow condition.

Other aspects and advantages of the invention will become apparent from the following detailed description, taken in conjunction with the accompanying drawings, which illustrate, by way of example, principles of the invention.

BRIEF DESCRIPTION OF THE DRAWINGS

FIG. 12 shows the operation of the door handle in the disengaged position where it is moving into engagement with the flow stop, also showing the platen in engagement with the release tab of the flow stop;

FIG. 13 shows the door in contact with the platen and shows the door handle being closed against the door and coming into engagement with the flow stop to move it to the flow configuration;

FIG. 14 shows the door handle moving the flow stop to the flow configuration with the sear of the handle moving into position to engage the flow stop;

FIG. 15 shows the flow stop placed into the flow configuration and the hook of the sear of the handle fully engaged with the slide clamp of the flow stop so that when the handle and door are opened, the sear will pull the slide clamp of the flow stop into the occluding configuration;

DETAILED DESCRIPTION OF PREFERRED EMBODIMENTS

Figure 1:
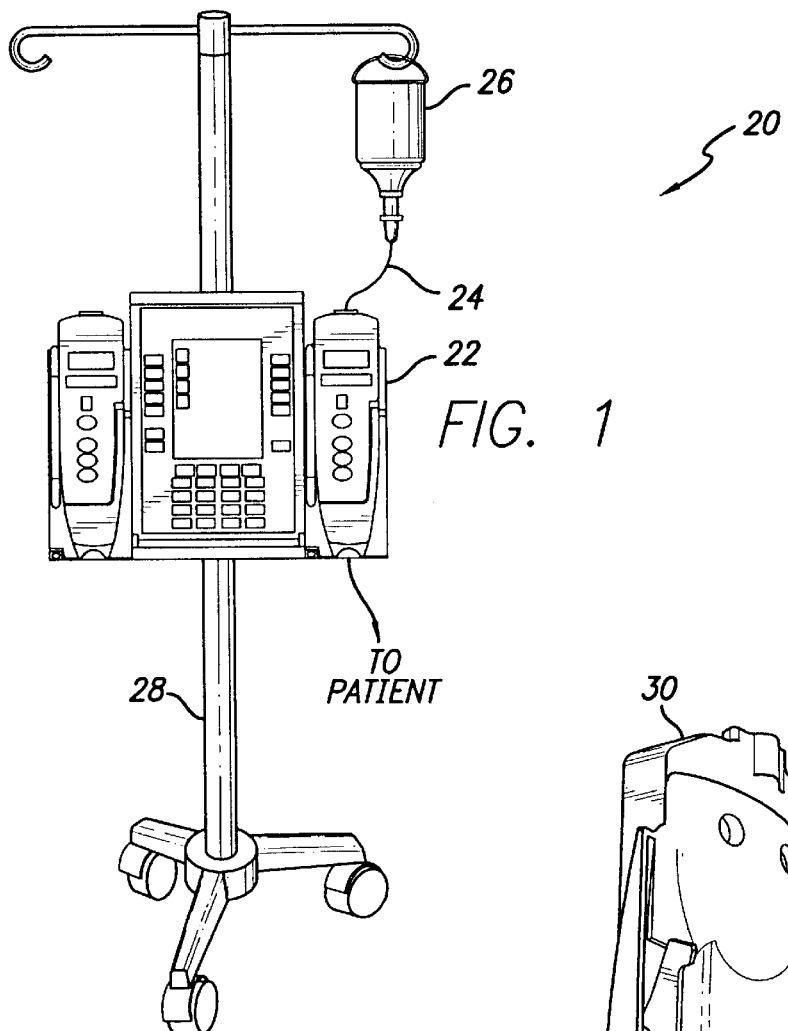
FIG. 1 is a front view of a medical instrument having two medical fluid infusion pumps, one of which is connected to a fluid reservoir for pumping the contents of the fluid reservoir to a patient.

Referring now to the drawings in which like reference numerals indicate like or corresponding element among the views, there is shown in FIG. 1 a patient management system 20 having an infusion pump 22 in operative engagement with an intravenous ("IV") administration tube 24. A fluid source 26 can be suspended from appropriate apparatus such as an IV pole 28. The tube 24 is connected between the fluid source 26 and the patient (not shown) so that the patient may receive the fluid of the fluid source at a rate controlled by the infusion pump 22.

Figure 2:
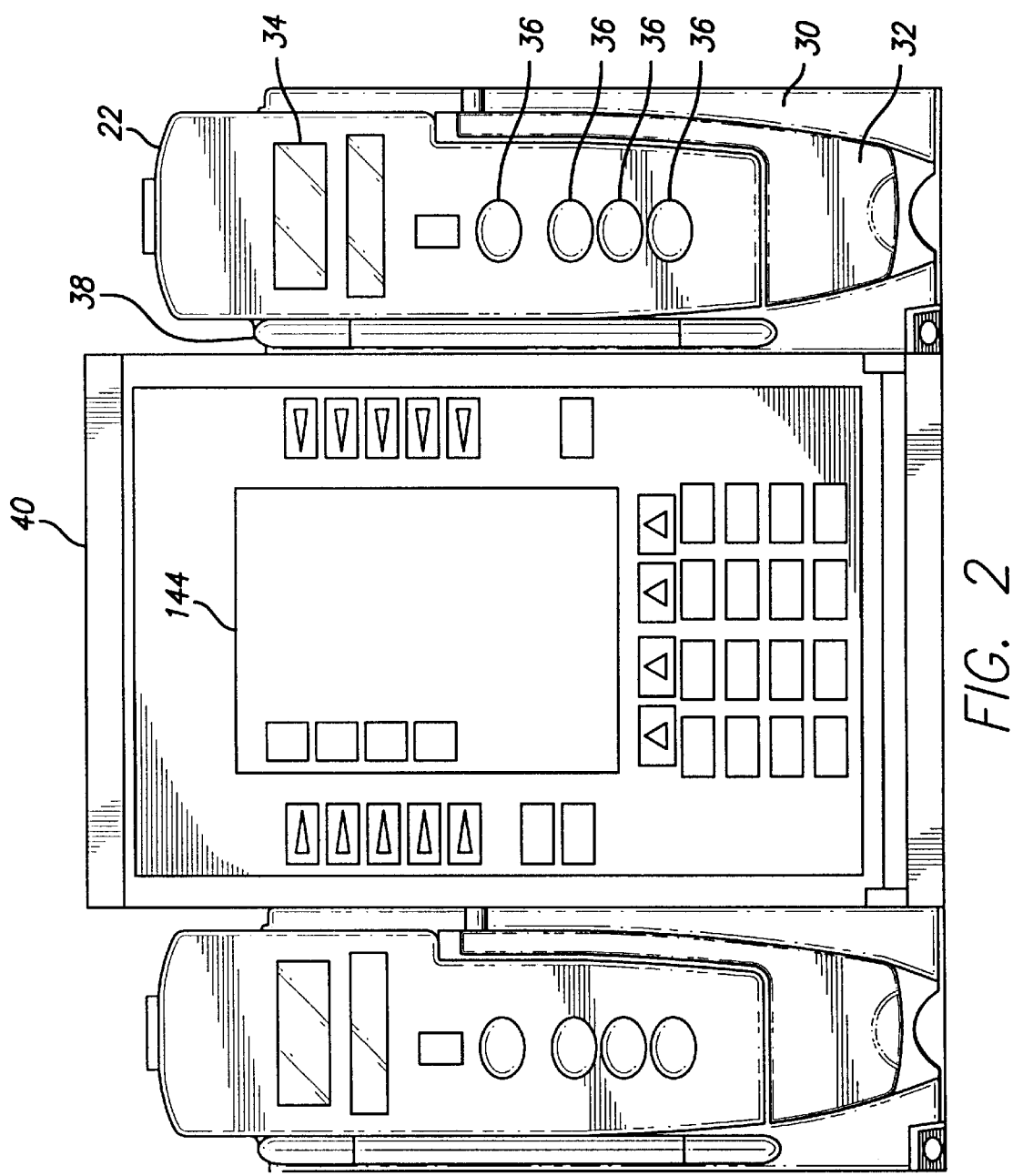
FIG. 2 is an enlarged view of the medical instrument of FIG. 1 showing the front doors and pivoting handles of both fluid infusion pumps.

Referring now to FIG. 2, an enlarged view of the front of the infusion pump 22 is shown. The pump includes a front door 30 and a handle 32 that operates to lock the door in a closed position. A display, such as an LED display, exists on the door in this embodiment and may be used to display various information relevant to the pump, such as alerting messages. Control keys 36 exist for programming the infusion pump as desired. The front door is shown connected to the housing of the pump by means of a first hinge 38. As is apparent from FIGS. 1 and 2, the hinge 38 of the door must be placed far enough forward so that the door 30, which opens from right to left in the figures, can clear the device or module to which the pump is attached. This hinge placement permits the pump 22 to be streamlined in size yet it can be connected on its left or right side to another module. In the example shown, an advanced programming module 40 is attached to the left side of the infusion pump 22. Other devices or modules, including another infusion pump, may be attached to the right side of the infusion pump 22 shown. The first hinge 38 will permit the modules to be opened without interfering with the adjacent module.

Figure 3:
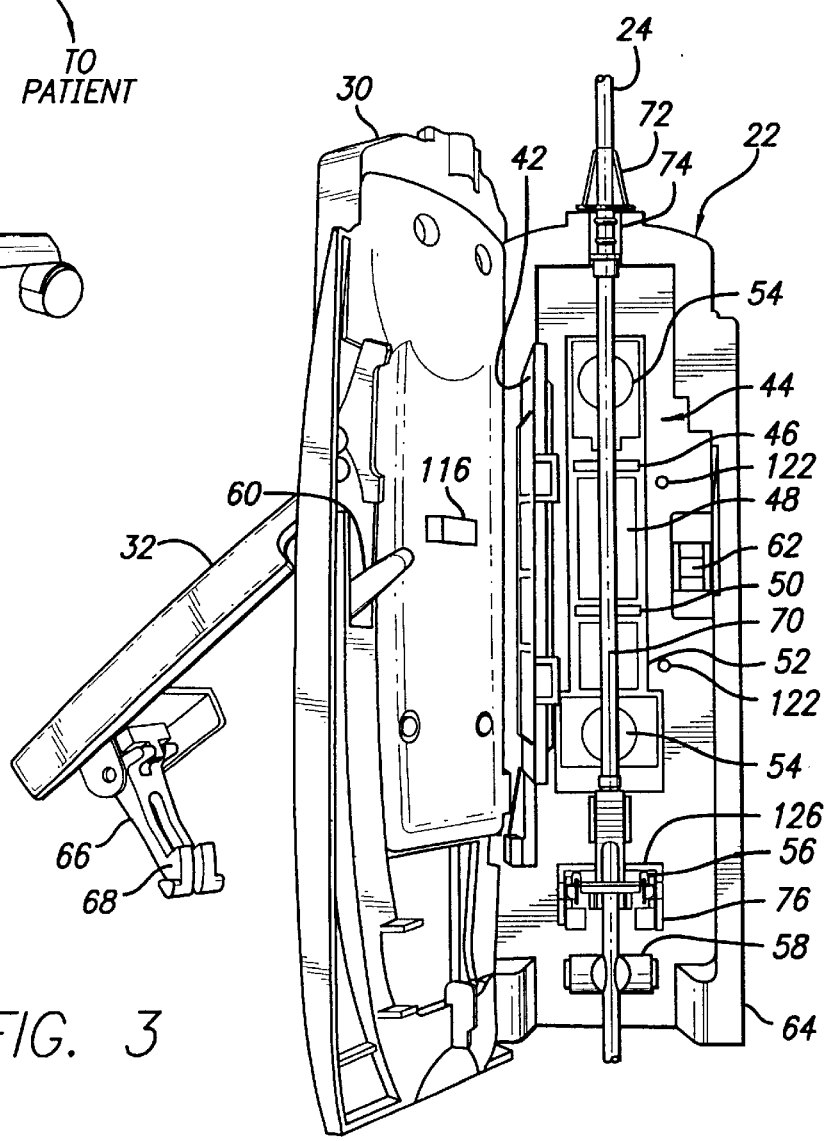
FIG. 3 is view of one of the fluid infusion pumps of FIGS. 1 and 2 with the door in the open position and showing details of a platen, a pumping mechanism, a fluid infusion tube in position in relation to that mechanism, and also showing a fluid flow stop formed as an integral part of the tube in position in the housing of the pump, and also showing a pivoting handle on the door of the pump used to secure the door in the closed position shown in FIGS. 1 and 2 and also used to move the flow stop to the occluded configuration when the door is opened.

Turning now to FIG. 3, the infusion pump 22 of FIGS. 1 and 2 is shown in perspective view with the front door 30 open. A platen 42 is mounted between the door 30 and the pumping mechanism 44. In this case, the pumping mechanism 44 is of the "four finger" type and includes an upstream occluder 46, a primary pumping finger 48, a downstream occluder 50, and a secondary pumping finger 52. The operation of four finger pumps is well known to those skilled in the art and no further operational details are provided here.

Upstream and downstream of the pumping mechanism 44 are included pressure sensors 54. The IV tube 24 also includes a flow stop 56 and the pump 22 also includes an air-in-line sensor 58. The handle 32 includes a latch arm 60 positioned to engage a yoke 62 located on the housing 64 of the pump. Engagement of the yoke by the latch arm will permit the door to remain locked in the closed position. The handle 32 also includes a sear 66 having at least one hook 68, and in the embodiment show, the sear has two hooks.

As further shown in FIG. 3, IV tube 24 and its associated pumping segment 70 are mounted across the pumping mechanism 44 by the engagement of an upstream fitment 72 with an upper bracket 74 and the engagement of the flow stop 56 with a lower flow stop bracket 76. When the IV tube 24 is engaged with the pump 22, the pumping segment 70 is positioned against the pumping mechanism 44. Also, with this engagement, the pumping segment 70 is placed under slight tension between the upstream fitment 72 and the flow stop 56 to ensure a snug fit between the pumping segment 70 and the four finger pumping mechanism 44.

Figure 4:
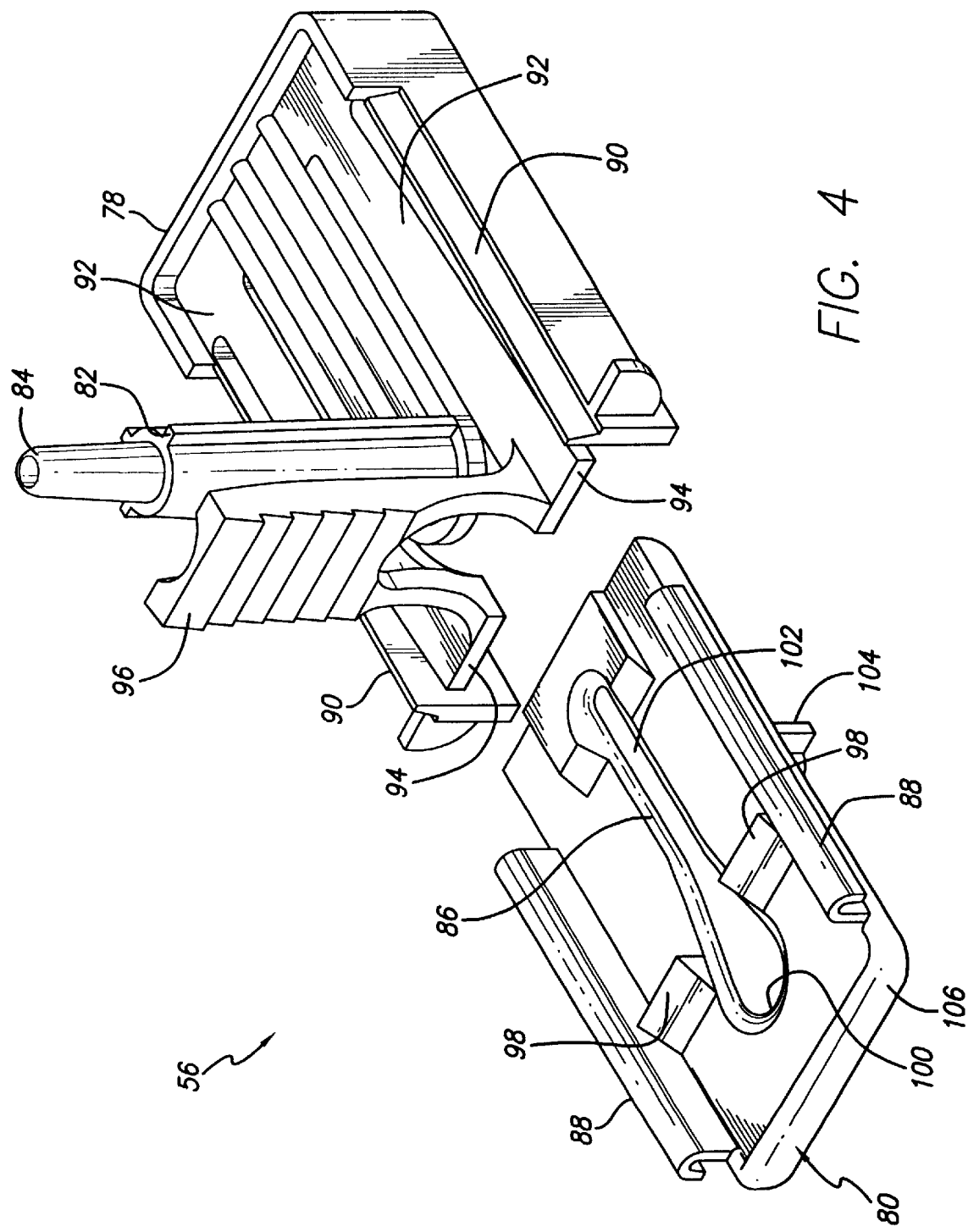
FIG. 4 is a perspective view of a flow stop device showing a slide clamp and a base, the base having a locking arm and a release tab.

Referring now to FIG. 4, the flow stop 56 is shown in more detail. The flow stop 56 consists generally of a relatively open, box shaped base 78 and a mating slide clamp 80. Both parts can be formed by injection molding from various plastic materials. The solid rectangular body of the slide clamp 80 is shaped and sized to fit slidingly within the base 78. The base 78 has a tower 82 formed on the top surface of the base with the tower 82 extending upwardly from the base 78 substantially perpendicular to the base. The top end of the tower is formed as a male tube connector 84 over which a pumping tube can be attached. The open bottom end of the tower 82 is attached to the base 78 and it is formed as a female tube connector into which an IV tube can be attached. The IV tube and the pumping tube can be the same tube if desired, simply passing through the tower 82.

The slide clamp 80 includes an elongated aperture 86 and is oriented so that the elongated dimension of the aperture is arranged on the slide clamp to be parallel to the direction of the relative sliding movement between the base and the slide clamp. Two side edges of the body of the slide clamp are fitted with rails 88 that lie parallel to the direction of the relative sliding movement. When the slide clamp is slidingly engaged with the base 78, the rails 88 fit in a sliding fashion over two rail channels 90 in the top of the base and over two frames formed on the edge of the base. Alignment of the slide clamp 80 with the base 78 is accomplished by the fit of the rails 88 over the frames 90, and by the fit of the body of the slide clamp between the frames.

Two flexible cantilevered locking arms 92 are molded into the top of the base, with their distal free ends 94 biased downwardly below the top surface of the base. Biasing of the free ends 94 downwardly is accomplished by molding the locking arms in a downwardly sloped configuration, but the biasing could also be accomplished by the use of springs or other means. A release tab 96 is formed on the locking arms 92, projecting upwardly from the locking arms substantially parallel to the longitudinal axis of the tower 82. In the free state, when the locking arms are sloped downwardly relative to the top surface of the base, the release tab 96 is spaced away from the outer surface of the tower. The free ends of the locking arms can be flexed upwardly by pressing the release tab toward the tower. Without departing from aspects of the invention, one locking arm 92 can be used in place of the two shown, or each locking arm can have a separate release tab 96.

Two locking projections 98 are molded on the top surface of the slide clamp with the locking projections taking the form of ramps. The locking projections are transversely positioned on the slide clamp to align with the free ends 94 of the locking arms 92 when the slide clamp is inserted into the base. The locking projections are also longitudinally positioned to prevent the slide clamp from being inserted into the base far enough to move from its occluding position to its flow position.

As seen in FIG. 4, the elongated aperture 86 through the slide clamp 80 has an open end 100 shaped essentially as a round hole with a sufficiently large diameter to allow the tube to pass through the open end without being occluded. Preferably, the diameter of the open end 100 is large enough to allow the tube to remain unrestricted. The other end of the aperture is a relatively narrow slot 102. The width of the slot 102 is sufficiently small that the tube passing through the slot 102 would be completely occluded and would remain occluded against a foreseeable range of fluid pressures in the tube. The range of pressure against which the tube would remain occluded would include at least the static head anticipated during normal use of the infusion apparatus.

As seen in FIG. 4, the locking projections 98 project upwardly from the top surface of the slide clamp 80 presenting a substantially vertical locking face to engage the free ends 94 of the locking arms 92 when the slide clamp is in its occluding configuration. Referring now to FIGS. 4, 5, 6, 7, and 8, one or more pulling projections 104 project downwardly from the bottom surface of the slide clamp. Each of the pulling projections 104 presents a substantially vertical pulling face that will interact with the sear 66 of the door handle 32 (not shown) to pull the slide clamp 80 partially out of engagement with the base 78 into the occluded configuration (FIG. 7) before the door 30 (not shown) is opened. Pulling the slide clamp 80 partially out of the base 78 moves the slide clamp 80 from its open configuration (FIG. 8) to its occluding configuration (FIG. 7). The body of the slide clamp 80 also presents a substantially vertical pushing face 106 on one end, against which the door of the housing pushes to fully insert the slide clamp into the base when the door is closed. Pushing the slide clamp into full insertion with the base moves the slide clamp from its occluding configuration to its flow configuration.

Figure 5:
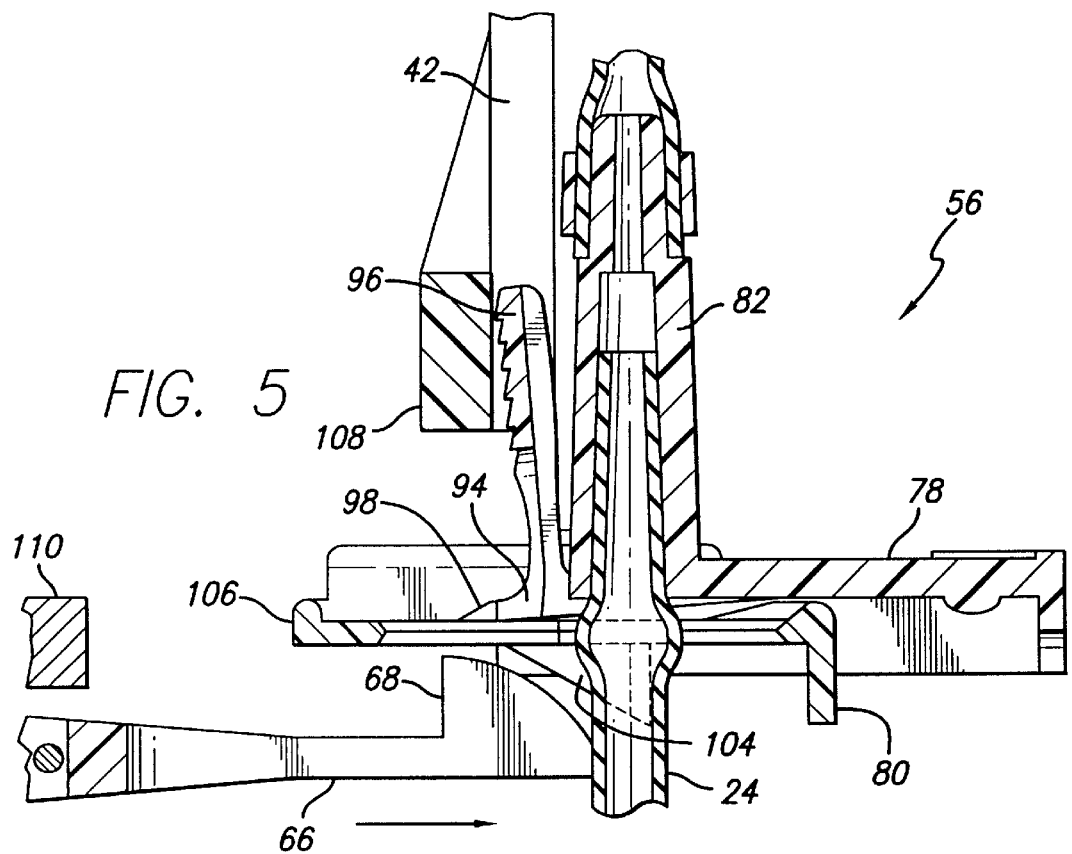
FIG. 5 shows the operation of the platen on the release tab of the flow stop, and the sear and hook of the door handle prior to the slide clamp of the flow stop being moved to the flow configuration.
Figure 6:
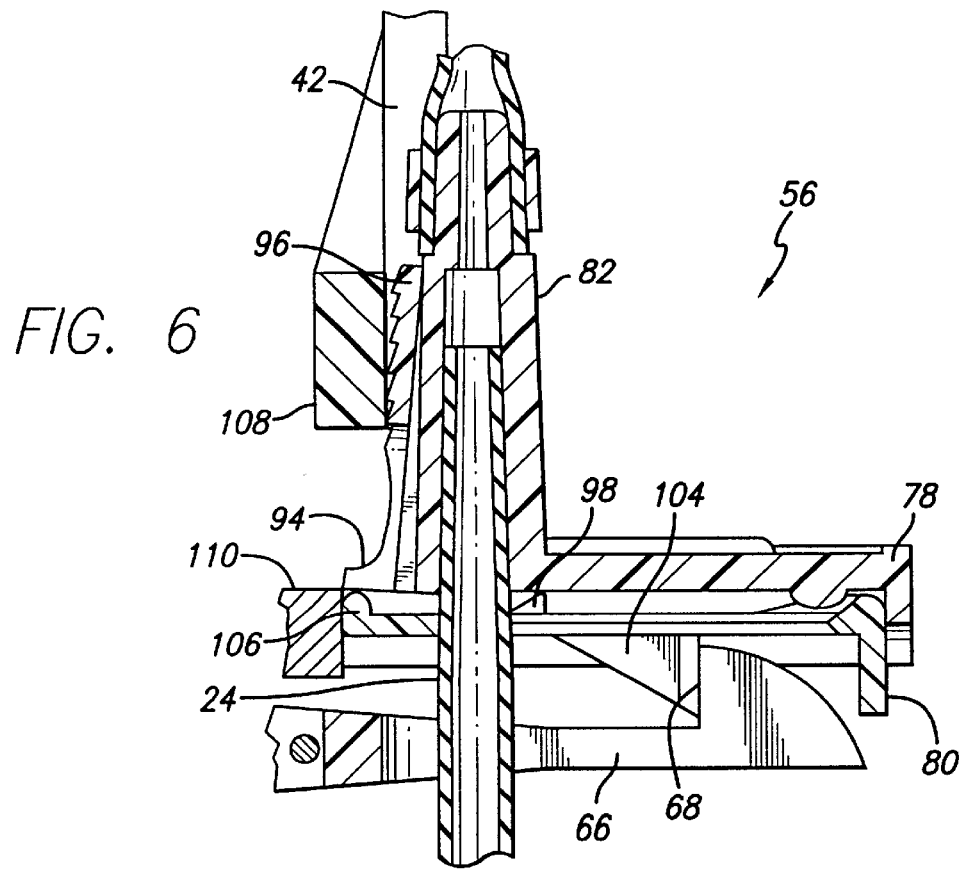
FIG. 6 shows the full engagement of the flow stop with the platen and the sear and hook of the door handle in position to return the slide clamp of the flow stop to the occluding position as the door is opened.
Figure 7:
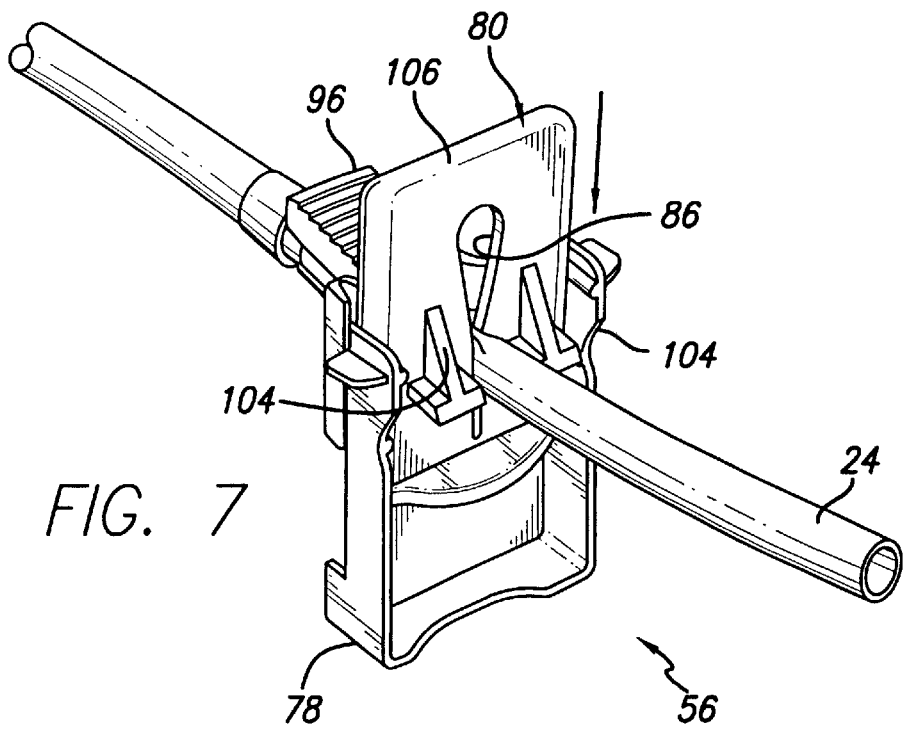
FIG. 7 is a perspective view of the flow stop in the occluding configuration showing its engagement with the tube.

FIGS. 5 and 6 show in general how the flow stop 56 interacts with the platen 42. FIG. 5 shows the slide clamp 80 in its occluding configuration relative to the base 78 with the slide clamp partially withdrawn from the base and the free ends 94 of the locking arms engaging the locking projections 98 to hold the slide clamp in its occluding configuration. This position of the slide clamp is achieved before the door is opened and maintained until after the door is closed. FIG. 6 shows the slide clamp in its flow configuration with the slide clamp fully inserted within the base and the free ends 94 of the locking arms 92 flexed upwardly a sufficient amount to clear the locking projections 98.

Figure 8:
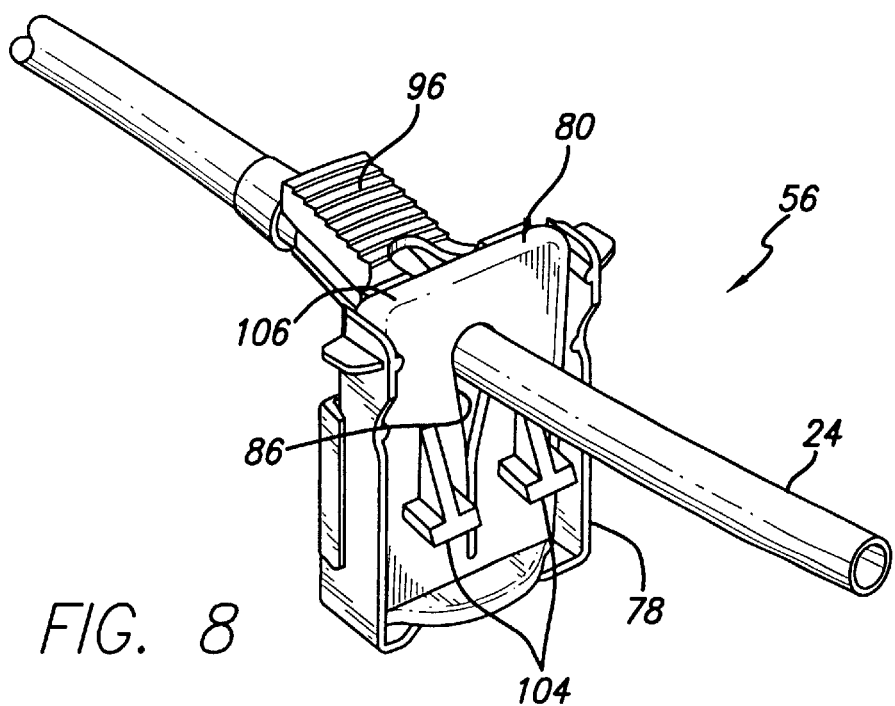
FIG. 8 is a perspective view of the flow stop in the flow configuration showing its engagement with the tube.

Operative elements are shown schematically in FIGS. 5 and 6. A flow stop actuator portion 108 of the platen 42 is positioned to contact the release tab 96 as the door is moved to the closed position and to press the release tab toward the tower 82. A pushing boss 110 formed on the handle (not shown) is positioned to contact the pushing face 106 on the slide clamp 80 as the handle is engaged to push the slide clamp from its occluding configuration (FIG. 7) to its flow configuration (FIG. 8). Finally, one or more pulling hooks 68 are formed on the sear 66 and are positioned to contact the pulling projections 104 as the handle is disengaged from the door to open the door and pull the slide clamp 80 from its flow configuration to its occluding configuration.

Further details of the flow stop 56 may be obtained from U.S. Pat. No. 5,453,098 which is incorporated herein by reference. Additionally, such a flow stop is available from ALARIS Medical Systems, Inc. under the trademark Flo-Stop®.

Figure 9:
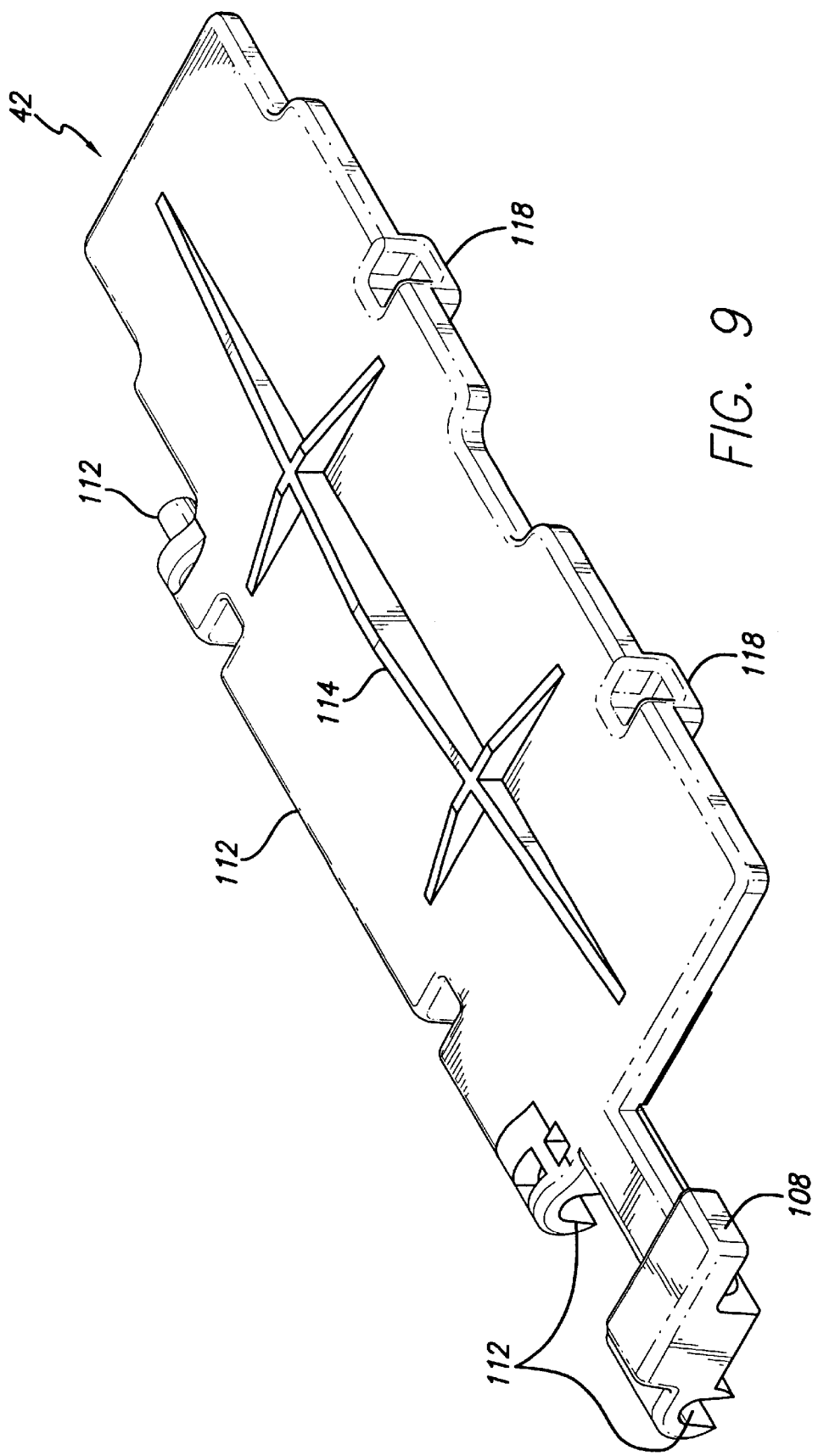
FIG. 9 is a perspective view of a platen in accordance with aspects of the invention.

Referring to the platen 42 shown in FIG. 9, a body portion 112 includes an extension located and dimensioned to act as a flow stop actuator portion 108. It should be noted that the actuator portion 108 is offset from the body portion and is separately hinged 112 for support. It is offset to make necessary contact with the release tab 96 of the flow stop (FIG. 6) so that the flow stop 56 may be moved to its flow configuration (FIG. 8). The platen also includes a series of interconnected raised ribs that distribute the load provided by the closed door. In particular, there is a raised load distribution rib 114 interconnected with the series of ribs to make contact with the inner surface of the door, and in particular, with a pressure surface 116 (FIG. 3) mounted or formed on the inner surface of the door. This feature is shown in further detail in conjunction with drawings discussed below. The platen also includes a plurality of contact datum surfaces 118 (two of which may be seen in FIG. 9) disposed on the platen at positions selected to engage datum pins formed on the pumping mechanism bezel, as will be discussed in more detail below. The surfaces 118 permit the platen to be precisely located a desired distance away from the pumping mechanism 44 when the door 30 is closed. In one embodiment, the platen was formed of thermoset material having a low creep value. One such material is a glass-filled liquid crystal polymer (LCP).

As shown in FIGS. 1 and 2, the door 30 of the pump is mounted forward to a degree that permits the infusion pump to be mounted closely adjacent to other such devices. Because of this door mounting feature, close side-by-side mounting of devices may be achieved yet their front doors may be opened for access without interfering with operation of the adjacent devices. However, such forward door mounting results in a configuration where the door is at an unacceptable angle to the fluid tube 24. If the inner surface of the door were attempted to be used to operate as a platen to the pumping mechanism, it would tend to roll the tube 24 out of position as the door is closed. Instead, in accordance with an aspect of the invention, a separate platen is used and is mounted on a separate hinge closer to the pumping mechanism. The separate or second hinge permits placement of the platen in relation to the pumping mechanism to minimize lateral displacement of the tube (rolling of the tube) as the door closes. As will be seen below, a set of datum pins formed on the bezel of the pumping mechanism and a counterpart set of contact datum surfaces 118 formed on the platen permit accurate placement of the platen in relation to the pumping mechanism. Consequently, a less precise, lower tolerance "floating hinge" 112 may be used to mount the platen to the housing. Tolerances are controlled solely during molding of the datum pins on the bezel and the contact datum surfaces of the platen.

Figure 10:
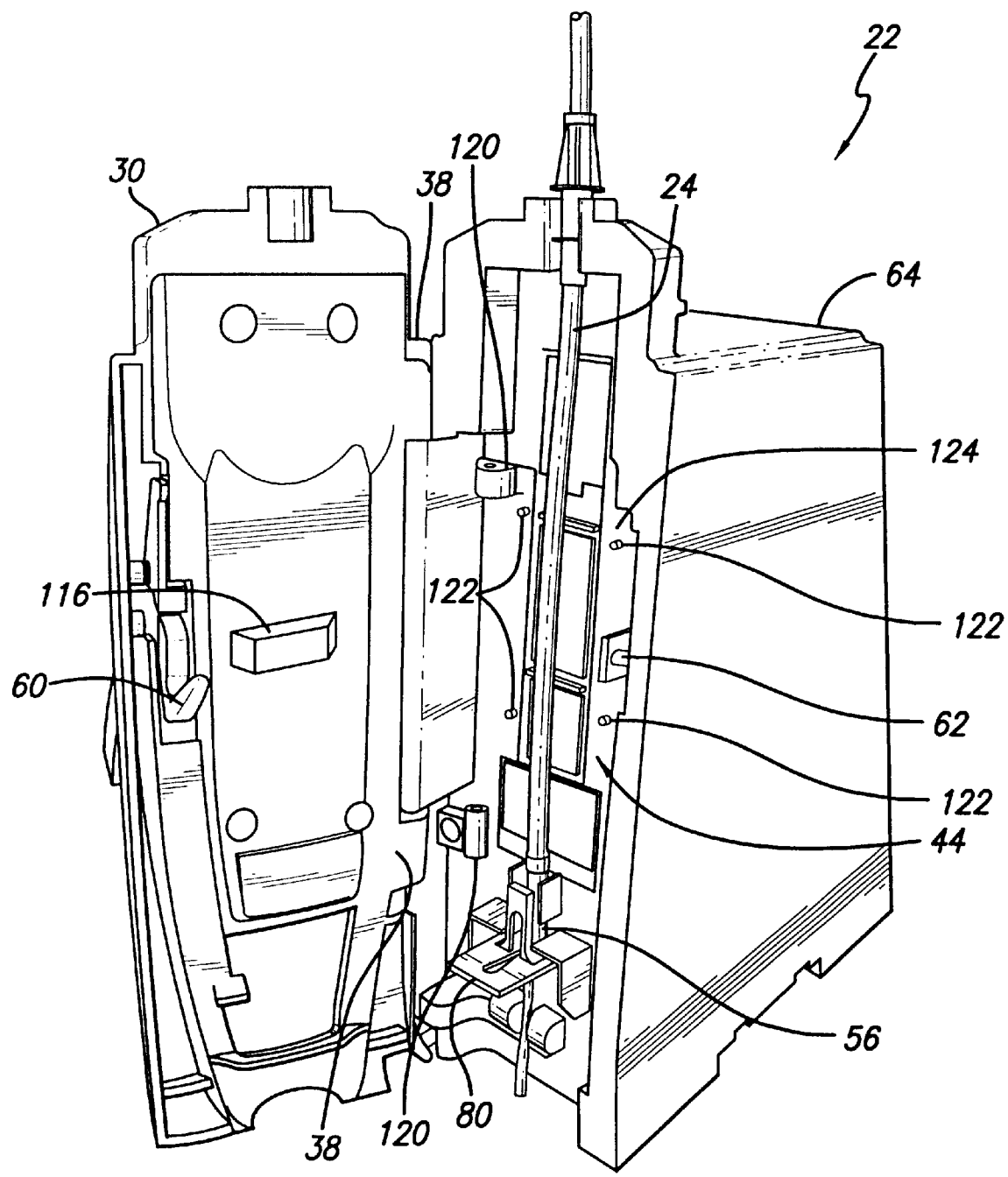
FIG. 10 is a perspective view of the front of an infusion pump of FIGS. 1 through 3 with the platen removed so that the hinge of the door may be seen and the engagement surface of the door that contacts the platen to exert pressure on the platen, also shown in the floating hinge of the platen.

Referring now to FIG. 10, a perspective view of the pump 22 is shown with the platen removed so that the hinge of the outer door 30 may be seen. The housing floating hinge 120 can be seen and is used to receive the counterpart hinge of the platen. Also shown are four datum pins 122 located on the bezel 124 surrounding the pumping mechanism 44. Although not shown, the yoke 62 is spring biased towards the housing 64. The spring (not shown) force is strong enough to hold the door 30 closed against the platen such that the platen applies enough pressure against the tube 24 so that the pumping mechanism is always occluding the tube once engaged. The spring force is also strong enough to keep the platen against the datum pins 122 during use of the pump, regardless of the pressure of the fluids pumped through the tube 24.

Figure 11:
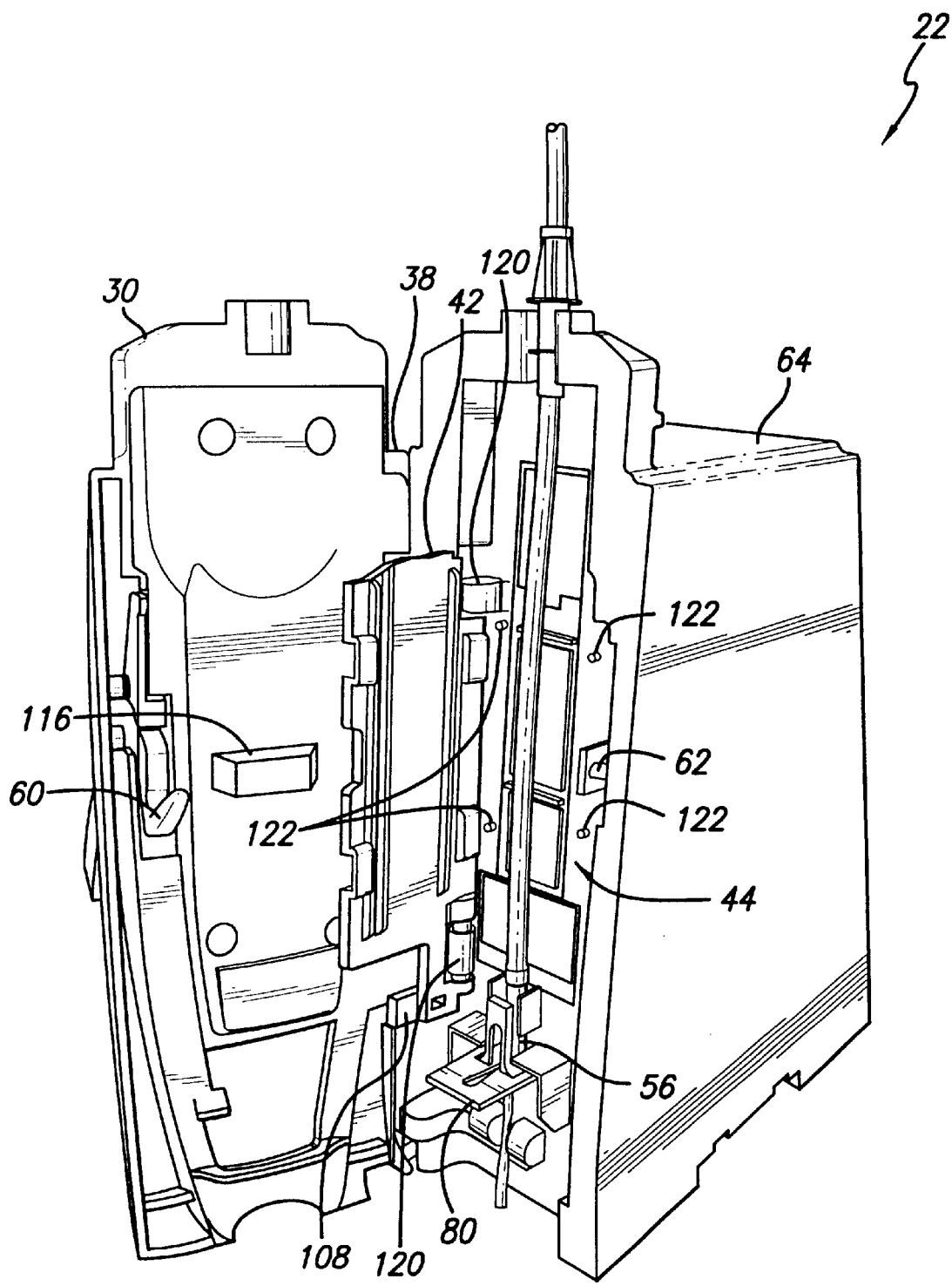
FIG. 11 is also a front perspective view of an infusion pump of FIGS. 1 through 3 with the platen in place on its floating hinge, and showing the datum pins on the bezel of the pumping mechanism and the contact datum surfaces of the platen positioned to engage the pins.

FIG. 11 is identical to FIG. 10 except that the platen 42 is shown in position in the pump. The first hinge 38 with which the door 30 is mounted to the pump is more forward that the second hinge 120 with which the platen is mounted to the pump. The yoke 62 is clearly visible and the latch arm 60 of the handle which is used to engage the yoke to hold the door in the closed position. The datum pins 120 are also visible.

FIGS. 12 through 15 present the operation of the door handle and its specific components in controlling the configuration of the flow stop 56. As the pivoting handle 32 captures the yoke 62 with the latch arm 60, the sear 66 and pushing boss 110 are moved toward the flow stop 56, as shown in FIG. 12. It will be noted that the flow stop actuation portion 108 of the platen 42 has already engaged the release tab 96 of the flow stop base 78 and moved it to the released position. Although not shown, the platen has already engaged the tube 24 with the pumping mechanism 44 so that the tube has become occluded by the pumping mechanism. Thus free flow through the tube is not possible. The slide clamp 80 of the flow stop may now be moved to the flow configuration. FIG. 13 presents more detail of the platen 42 showing the pressure distribution rib 114 in contact with the door pressure surface 116. The sear has begun moving into position beneath the slide clamp but the pushing boss 110 has not yet come into contact with the pushing face of the slide clamp 80.

FIG. 14 shows the pushing boss 110 in contact with the pushing face 106 of the slide clamp and pushing the slide clamp from the occluding configuration to the flow configuration. Finally, FIG. 15 shows the handle fully engaged with the housing thereby locking the door in the closed position. The slide clamp 80 has been fully moved into the base 78 of the flow stop 56 and into the flow configuration. Flow is now fully controlled by the pumping mechanism. The hook 68 of the sear 66 has engaged the pulling projection 104 of the slide clamp so that once the handle is pulled outward to open the door, the hook of the sear will first move the slide clamp to the occluding configuration as shown in FIG. 12 thus preventing free flow once the pumping mechanism is disengaged from the tube once the door is opened.

Figure 16:
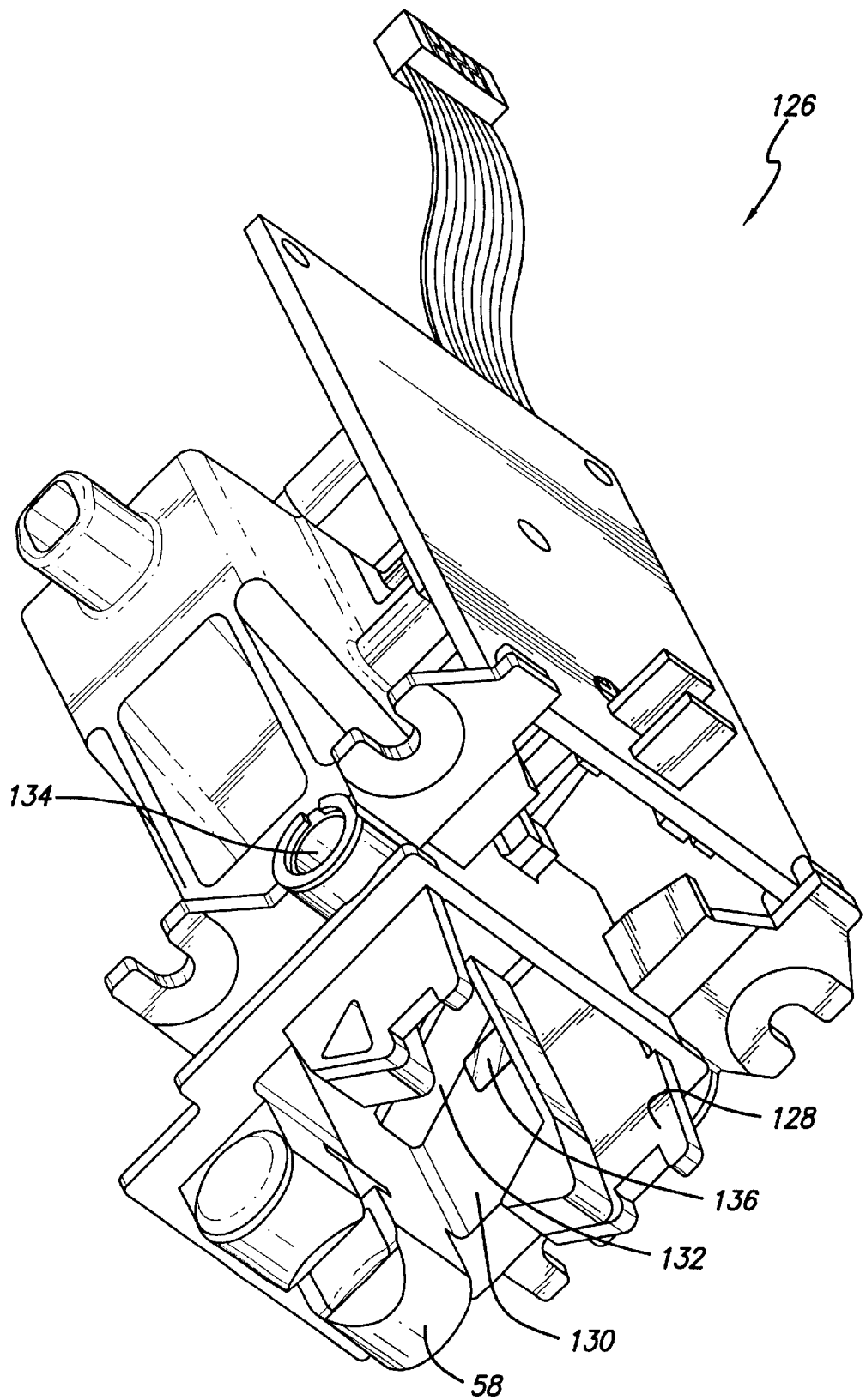
FIG. 16 is a perspective view of the housing of the flow stop mounting portion of the infusion pump showing a sear detector and showing part of a flow stop detector.

Turning now to FIG. 16, a sensor module 126 is shown. The placement of the module in the infusion pump is shown in FIG. 3 by numeral 126. The module includes a flow stop mounting slot 128 into which the flow stop is slid during the process of mounting the tube 24 to the pump 22. This is also shown in FIG. 3. Shown also in FIG. 16 is the air-in-line sensor 58 that is included in the sensor module 126. The sensor module also includes a sear slot 130 into which the sear 66 of the handle moves as the door is closed. The sear slot 130 also includes guide ramps 132 (only one of which can be seen) that assist in forcing the hooks 68 of the sear 66 into contact with the pulling projections 104 of the slide clamp 80 (see FIG. 6).

The module 126 includes a flow stop detector apparatus mounted in conjunction with the flow stop mounting slot 128. In particular, the flow stop detector apparatus includes an emitter 134 mounted on one side of the flow stop slot 128 and a receiver (not shown) mounted on the opposite side of the flow stop slot 128. Placing the flow stop properly into the flow stop slot 128 will break the beam between the emitter and the receiver thereby indicating the presence of a flow stop.

Figure 17:
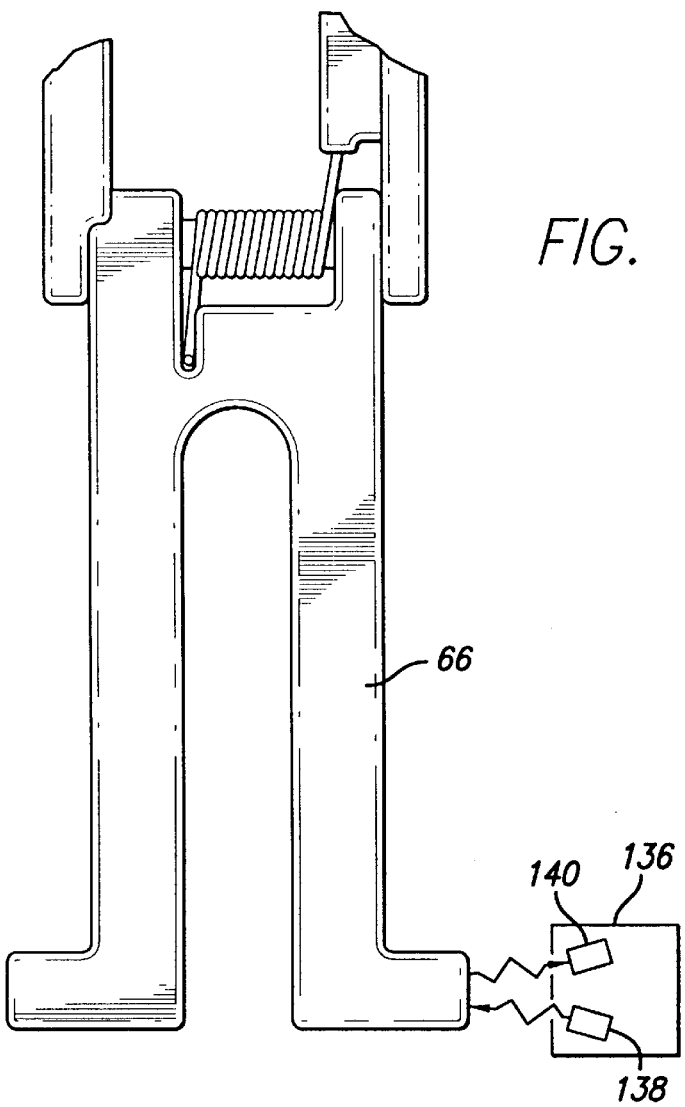
FIG. 17 shows in schematic fashion the operation of the reflective sear detector of one embodiment.

The module 126 also includes a sear detector 136 mounted so as to detect the presence of a sear. In this case, the sear detector is reflective in construction and is shown in schematic form in FIG. 17. The sear detector 136 includes an emitter 138 and a receiver 140. When a sear 66 is present, the beam from the emitter 138 will be reflected by the sear to the receiver 140 indicating the presence of a sear. As shown in schematic form, the emitter and receiver are pointed or "focused" to a particular location at which a sear is expected. To assist in detection, the sear is either formed of a reflective material, such as polymer having a reflective pigment, or is coated with a reflective material. Detecting the presence of the sear 66 also indicates that the door is closed and latched because it is highly unlikely that the sear could be detected by the sear detector 136 unless such a door configuration exists.

The sensor module provides two systems to avoid a free flow condition. The first system checks for the very existence of a flow stop, and the second system checks for the existence of a sear that can activate the flow stop to the occluding configuration when the door is opened. If either detector indicates the nonexistence of the respective item, the operator can be notified that a possible free flow condition could occur if the door of the pump is opened. The operator may then apply a manual clamp to the tube 24 downstream of the pump before the pump door is opened to manually avoid a free flow condition.

Figure 18:
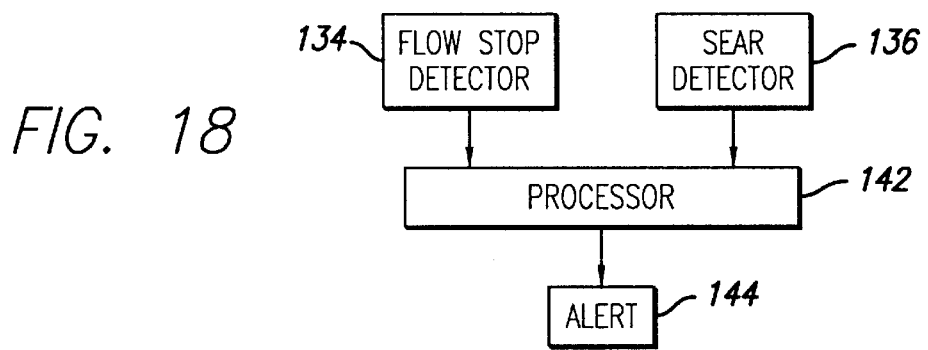
FIG. 18 is a schematic diagram of the sear detector and flow stop detector circuits connected to a processor to provide an alert if the respective sear and flow stop are not present.

A system using the flow stop detector and the sear detector is shown in FIG. 18. A processor 142 monitors the sear detector 136 and the flow stop detector 134 (numeral 134 is used to collectively indicate the flow stop detector here) and if either indicates that the respective component is not present, the processor may provide an alert 144. Such an alert may take a visual form or an audible form or both. A visual alert may be provided on the display 34 of the infusion pump itself or elsewhere, such as a display 144 of an advanced programming module 40 (see FIG. 2).

While embodiments of the invention have been illustrated and described, it will be apparent that various modifications can be made without departing from the spirit and scope of the invention. Accordingly, it is not intended that the invention be limited, except as by the appended claims.

What is claimed is:

1. An apparatus for controlling a flow stop to reside in an occluding configuration at which the flow stop occludes a resilient tube and to reside in a flow configuration at which the flow stop permits flow through the resilient tube, by the position of a door that is mounted with a first hinge to the housing of a medical instrument, the apparatus comprising:
   a base on the flow stop for holding the resilient tube;
   a slide clamp slidably mounted on said base and engaging the tube, the slide clamp adapted for movement between the occluding configuration and the flow configuration; and
   a platen mounted in relation to the housing with a second hinge, the second hinge located closer to the tube than the first hinge is located to the tube such that the platen is disposed between the door and the slide clamp of the flow stop wherein moving the door towards the housing engages the platen and engages the slide clamp to move the slide clamp to the flow configuration whereby fluid may flow through the tube.

2. The apparatus of claim 1 wherein the platen comprises a body portion and a flow stop actuator portion disposed as an extension of and offset from the body portion of the platen such that the body portion of the platen engages the tube against the medical instrument while being pivoted into position by the movement of the door and the actuator portion contacts the flow stop before the slide clamp may be moved to the open position.

3. The apparatus of claim 2 wherein:
   the flow stop comprises a locking arm engaged with the slide clamp that prevents the slide clamp from being moved to the flow configuration; and
   the flow stop comprises a release tab connected to the locking arm that disengages the locking arm from the slide clamp when the release tab is moved to a released position;
   wherein the flow stop actuator portion of the platen is disposed so as to contact the release tab of the flow stop and move it to the released position before the slide clamp is moved to the flow configuration.

4. The apparatus of claim 2 wherein:
   the medical instrument includes datum pins located at selected positions on the instrument, the pins having a predetermined length selected so that when the platen is engaged with the pins, the platen will have a known location in relation to the medical instrument; and
   wherein the length of the datum pins is selected so that the flow stop actuator portion of the platen will contact the release tab of the flow stop.

5. The apparatus of claim 4 wherein the second hinge of the platen comprises a floating hinge adapted to permit the platen to be located in contact with all the datum pins when the door engages the platen.

6. The apparatus of claim 4 wherein the platen comprises a plurality of contact datum surfaces disposed on the platen at positions selected to engage the datum pins when the door positions the platen in contact with the datum pins.

7. The apparatus of claim 4 wherein:
   the platen comprises a load distribution rib located on the platen so as to receive pressure from the door and distribute that pressure along the platen; and
   the door comprises a pressure surface located on the inside of the door at a location so as to contact the load distribution rib of the platen to press the platen against the datum pins.

8. The apparatus of claim 7 wherein:
   the housing of the medical instrument comprises an anchor yoke that is biased toward the housing;
   the door comprises a pivotally mounted handle located to engage and capture the anchor yoke to firmly hold the door in a closed position against the housing; and
   wherein the anchor yoke is biased towards the housing by an extent that will assure that the door contacts the load distribution rib of the platen thereby forcing the platen into contact with the datum pins.

9. The apparatus of claim 8 wherein the handle includes a sear with a hook, the sear and hook located so as to engage the slide clamp of the flow stop when the door is in the closed position and to move the slide clamp to the occluding configuration when the door of the medical instrument is opened thereby preventing free flow through the tube.

10. The apparatus of claim 9 further comprising:
    a sear detector located in the medical instrument at a position selected so as to detect the presence of the sear in position in relation to the slide clamp, the detector providing a sear detection signal; and
    a processor connected to the sear detector to receive the sear detection signal and adapted to provide a sear alert signal in the event that the sear is not detected by the sear detector.

11. The apparatus of claim 10 wherein the sear detector comprises a photo emitter and photo receiver both directed towards a predetermined location for the sear and the sear comprises a photo-reflective surface.

12. The apparatus of claim 9 further comprising:
    a flow stop detector located in the medical instrument at a position selected so as to detect the presence of the flow stop in the medical instrument and configured to provide a flow stop detection signal; and
    a processor connected to the flow stop detector to receive the flow stop detection signal and adapted to provide a flow stop alert signal in the event that the flow stop is not detected by the flow stop detector.

13. The apparatus of claim 1 wherein the first hinge is located forward on the housing so that the door is separated from the flow stop when the flow stop is mounted in the medical instrument.

14. An apparatus for controlling a flow of fluid through a tube mounted in a medical instrument, the medical instrument including a flow mechanism that engages the tube to precisely regulate the flow of fluid through the tube to a patient, and a flow stop mounted to the medical instrument, the flow stop having an occluding configuration at which the flow stop occludes the tube and a flow configuration at which the flow stop permits flow through the tube, the medical instrument having a housing to which a door is mounted with a first hinge, the apparatus comprising:

a base on the flow stop for holding the tube;

a slide clamp slidably mounted on said base and engaging the tube, the slide clamp adapted for movement between the occluding configuration and the flow configuration; and a platen mounted in relation to the housing with a second hinge, the second hinge located closer to the tube than the first hinge is located to the tube such that the platen is disposed between the door and the flow mechanism and the flow stop such that when the door is moved towards the flow mechanism, the door engages the platen causing the platen to engage the tube against the flow mechanism to occlude the tube by the flow mechanism and engages the slide clamp of the flow stop to move the slide clamp to the flow configuration thereby avoiding a free flow condition.

15. The apparatus of claim 14 wherein:

the flow stop comprises a locking arm engaged with the slide clamp that prevents the slide clamp from being moved to the flow configuration;

the flow stop comprises a release tab connected to the locking arm that disengages the locking arm from the slide clamp when the release tab is moved to a released position;

wherein the flow stop actuator portion of the platen is disposed so as to contact the release tab of the flow stop and move it to the released position before the slide clamp is moved to the flow configuration.

16. The apparatus of claim 15 wherein:

the pump includes datum pins located at selected positions near the flow mechanism, the pins having a predetermined length selected so that when the platen is engaged with the pins, the platen will have a known position in relation to the flow mechanism; and and wherein the length of the datum pins is selected so that the flow stop actuator portion of the platen will contact the release tab of the flow stop.

17. The apparatus of claim 16 wherein the second hinge of the platen comprises a floating hinge adapted to permit the platen to be located in contact with all the datum pins when the door engages the platen.

18. The apparatus of claim 16 wherein the platen comprises a plurality of contact datum surfaces disposed on the platen at selected positions to engage the datum pins when the door positions the platen in contact with the datum pins.

19. The apparatus of claim 16 wherein:

the platen comprises a load distribution rib located on the platen so as to receive pressure from the door and distribute that pressure along the platen; and the door comprises a pressure surface located on the inside of the door at a location so as to contact the load distribution rib of the platen to press the platen against the datum pins.

20. The apparatus of claim 16 wherein:

the housing of the medical instrument comprises an anchor yoke that is biased toward the housing;

the door comprises a pivotally mounted handle located to engage and capture the anchor yoke to firmly hold the door in a closed position against the housing; and wherein the anchor yoke is biased towards the housing by an extent that will assure that the door contacts the load distribution rib of the platen thereby forcing the platen into contact with the datum pins.

21. The apparatus of claim 20 wherein the handle includes a sear with a hook, the sear with hook located so as to engage the slide clamp of the flow stop when the door is in the closed position and to move the slide clamp to the occluding position when the door of the pump is opened before the platen moves away from the tube to permit the tube thereby preventing free flow through the tube.

22. The apparatus of claim 21 further comprising:

a sear detector located in the pump at a position selected so as to detect the presence of the sear in position in relation to the slide clamp, the detector providing a sear detection signal; and a processor connected to the sear detector to receive the sear detection signal and adapted to provide a sear alert signal in the event that the sear is not detected by the sear detector.

23. The apparatus of claim 22 wherein the sear detector comprises a photo emitter and photo receiver both directed towards a predetermined location for the sear and the sear comprises a photo-reflective surface.

24. The apparatus of claim 21 further comprising:

a flow stop detector located in the pump at a position selected so as to detect the presence of the flow stop in the infusion pump and configured to provide a flow stop detection signal; and a processor connected to the flow stop detector to receive the flow stop detection signal and adapted to provide a flow stop alert signal in the event that the flow stop is not detected by the flow stop detector.

25. The apparatus of claim 14 wherein the first hinge is located forward on the housing so that the door is separated from the flow stop when the flow stop is mounted in the medical instrument.

26. An apparatus for controlling the flow of fluid through a tube mounted in a medical fluid infusion pump, the pump including a pumping mechanism that engages the tube to precisely pump the fluid through the tube to a patient, the tube having a flow stop having a base and a slide clamp slidably mounted on the base and engaging the tube, the slide clamp having an occluding configuration at which the slide clamp occludes the tube and a flow configuration at which the slide clamp permits flow through the tube, the pump having a housing to which a door is mounted with a first hinge, the apparatus comprising:

a platen mounted in relation to the housing with a second hinge, the second hinge located closer to the tube than the first hinge is located to the tube such that the platen is disposed between the door and the pumping mechanism and the flow stop such that when the door is moved towards the pumping mechanism, the door engages the platen causing the platen to engage the tube against the pumping mechanism to occlude the tube by the pumping mechanism and engages the slide clamp of the flow stop to move the slide clamp to the flow configuration thereby avoiding a free flow condition.

27. The apparatus of claim 26 wherein the platen comprises a body portion and a flow stop actuator portion disposed as an extension of and offset from the body portion of the platen such that the body of the platen engages the tube against the pumping mechanism while being pivoted into position by the movement of the door and the actuator portion contacts the flow stop before the slide clamp may be moved to the open position.

28. The apparatus of claim 27 wherein:

the flow stop comprises a locking arm engaged with the slide clamp that prevents the slide clamp from being moved to the flow configuration;

the flow stop comprises a release tab connected to the locking arm that disengages the locking arm from the slide clamp when the release tab is moved to a released position;

wherein the flow stop actuator portion of the platen is disposed so as to contact the release tab of the flow stop and move it to the released position before the slide clamp is moved to the flow configuration.

29. The apparatus of claim 26 wherein:

the door comprises a pivotally mounted handle located to engage the housing to hold the door in a closed position thereby locking the platen against the tube which is against the pumping mechanism and thereby holding the flow stop in the flow configuration; and the handle includes a sear with a hook, the sear with hook located so as to engage the slide clamp of the flow stop when the door is in the closed position and to move the slide clamp to the occluding position when the door of the pump is opened before the platen moves away from the tube to permit the tube thereby preventing free flow through the tube.

30. The apparatus of claim 29 further comprising:

a sear detector located in the pump at a position selected so as to detect the presence of the sear in position in relation to the slide clamp, the detector providing a sear detection signal; and a processor connected to the sear detector to receive the sear detection signal and adapted to provide a sear alert signal in the event that the sear is not detected by the sear detector.

31. The apparatus of claim 30 wherein the sear detector comprises a photo emitter and photo receiver both directed towards a predetermined location for the sear and the sear comprises a photo-reflective surface.

32. The apparatus of claim 29 further comprising:

a flow stop detector located in the pump at a position selected so as to detect the presence of the flow stop in the infusion pump and configured to provide a flow stop detection signal; and a processor connected to the flow stop detector to receive the flow stop detection signal and adapted to provide a flow stop alert signal in the event that the flow stop is not detected by the flow stop detector.

33. The apparatus of claim 26 wherein:

the pump includes datum pins located at selected positions near the pumping mechanism, the pins having a predetermined length selected so that when the platen is engaged with the pins, the platen will have a known position in relation to the pumping mechanism; and and wherein the length of the datum pins is selected so that the flow stop actuator portion of the platen will contact the release tab of the flow stop.

34. The apparatus of claim 33 wherein the second hinge of the platen comprises a floating hinge adapted to permit the platen to be located in contact with all the datum pins when the door engages the platen.

35. The apparatus of claim 33 wherein the platen comprises a plurality of contact datum surfaces disposed on the platen at positions selected to engage the datum pins when the door positions the platen in contact with the datum pins.

36. The apparatus of claim 33 wherein:

the platen comprises a load distribution rib located on the platen so as to receive pressure from the door and distribute that pressure along the platen; and the door comprises a pressure surface located on the inside of the door at a location so as to contact the load distribution rib of the platen to press the platen against the datum pins.

37. An apparatus for controlling a flow stop to reside in an occluding configuration at which the flow stop occludes a resilient tube and to reside in a flow configuration at which the flow stop permits flow through the resilient tube, by the position of a door that is mounted with a first hinge to the housing of a medical instrument, the apparatus comprising:

a base on the flow stop for holding the resilient tube;

a slide clamp slidably mounted on said base and engaging the tube, the slide clamp adapted for movement between the occluding configuration and the flow configuration; and a platen mounted in relation to the housing with a second hinge, the first hinge located more forward in relation to the housing than the second hinge such that the platen is disposed between the door and the slide clamp of the flow stop wherein moving the door towards the housing engages the platen and engages the slide clamp to move the slide clamp to the flow configuration whereby fluid may flow through the tube.

38. The apparatus of claim 37 wherein the platen comprises a body portion and a flow stop actuator portion disposed as an extension of and offset from the body portion of the platen such that the body portion of the platen engages the tube against the medical instrument while being pivoted into position by the movement of the door and the actuator portion contacts the flow stop before the slide clamp may be moved to the open position.

39. The apparatus of claim 38 wherein:

the flow stop comprises a locking arm engaged with the slide clamp that prevents the slide clamp from being moved to the flow configuration; and the flow stop comprises a release tab connected to the locking arm that disengages the locking arm from the slide clamp when the release tab is moved to a released position;

wherein the flow stop actuator portion of the platen is disposed so as to contact the release tab of the flow stop and move it to the released position before the slide clamp is moved to the flow configuration.

40. The apparatus of claim 38 wherein:

the medical instrument includes datum pins located at selected positions on the instrument, the pins having a predetermined length selected so that when the platen is engaged with the pins, the platen will have a known location in relation to the medical instrument; and wherein the length of the datum pins is selected so that the flow stop actuator portion of the platen will contact the release tab of the flow stop.

41. The apparatus of claim 40 wherein the second hinge of the platen comprises a floating hinge adapted to permit the platen to be located in contact with all the datum pins when the door engages the platen.

42. The apparatus of claim 40 wherein the platen comprises a plurality of contact datum surfaces disposed on the platen at positions selected to engage the datum pins when the door positions the platen in contact with the datum pins.

43. An apparatus for controlling a flow stop to reside in an occluding configuration at which the flow stop occludes a resilient tube and to reside in a flow configuration at which the flow stop permits flow through the resilient tube, by the position of a door that is mounted with a first hinge to the housing of a medical instrument, the apparatus comprising:

a base on the flow stop for holding the resilient tube;

a slide clamp slidably mounted on said base and engaging the tube, the slide clamp adapted for movement between the occluding configuration and the flow configuration; and a platen mounted in relation to the housing with a second hinge, the second hinge located at a position different from the position of the first hinge but such that the platen is disposed between the door and the slide clamp of the flow stop wherein moving the door towards the housing engages the platen and engages the slide clamp to move the slide clamp to the flow configuration whereby fluid may flow through the tube, the platen comprising a load distribution rib located on the platen so as to receive pressure from the door and distribute that pressure along the platen;

wherein the medical instrument includes datum pins located at selected positions on the instrument, the pins having a predetermined length selected so that when the platen is engaged with the pins, the platen will have a known location in relation to the medical instrument; and wherein the door comprises a pressure surface located on the inside of the door at a location so as to contact the load distribution rib of the platen to press the platen against the datum pins.

44. The apparatus of claim 43 wherein the platen comprises a body portion and a flow stop actuator portion disposed as an extension of and offset from the body portion of the platen such that the body portion of the platen engages the tube against the medical instrument while being pivoted into position by the movement of the door and the actuator portion contacts the flow stop before the slide clamp may be moved to the open position.

45. The apparatus of claim 44 wherein:

the flow stop comprises a locking arm engaged with the slide clamp that prevents the slide clamp from being moved to the flow configuration; and the flow stop comprises a release tab connected to the locking arm that disengages the locking arm from the slide clamp when the release tab is moved to a released position;

wherein the flow stop actuator portion of the platen is disposed so as to contact the release tab of the flow stop and move it to the released position before the slide clamp is moved to the flow configuration.

46. The apparatus of claim 44 wherein the length of the datum pins is selected so that the flow stop actuator portion of the platen will contact the release tab of the flow stop.

47. The apparatus of claim 46 wherein the second hinge of the platen comprises a floating hinge adapted to permit the platen to be located in contact with all the datum pins when the door engages the platen.

48. The apparatus of claim 46 wherein the platen comprises a plurality of contact datum surfaces disposed on the platen at positions selected to engage the datum pins when the door positions the platen in contact with the datum pins.

49. The apparatus of claim 43 wherein:

the housing of the medical instrument comprises an anchor yoke that is biased toward the housing;

the door comprises a pivotally mounted handle located to engage and capture the anchor yoke to firmly hold the door in a closed position against the housing; and wherein the anchor yoke is biased towards the housing by an extent that will assure that the door contacts the load distribution rib of the platen thereby forcing the platen into contact with the datum pins.

50. The apparatus of claim 49 wherein the handle includes a sear with a hook, the sear and hook located so as to engage the slide clamp of the flow stop when the door is in the closed position and to move the slide clamp to the occluding configuration when the door of the medical instrument is opened thereby preventing free flow through the tube.

51. The apparatus of claim 50 further comprising:

a sear detector located in the medical instrument at a position selected so as to detect the presence of the sear in position in relation to the slide clamp, the detector providing a sear detection signal; and a processor connected to the sear detector to receive the sear detection signal and adapted to provide a sear alert signal in the event that the sear is not detected by the sear detector.

52. The apparatus of claim 51 wherein the sear detector comprises a photo emitter and photo receiver both directed towards a predetermined location for the sear and the sear comprises a photo-reflective surface.

53. The apparatus of claim 50 further comprising:

a flow stop detector located in the medical instrument at a position selected so as to detect the presence of the flow stop in the medical instrument and configured to provide a flow stop detection signal; and a processor connected to the flow stop detector to receive the flow stop detection signal and adapted to provide a flow stop alert signal in the event that the flow stop is not detected by the flow stop detector.

54. The apparatus of claim 43 wherein the first hinge is located forward on the housing so that the door is separated from the flow stop when the flow stop is mounted in the medical instrument.

\* \* \* \* \*